United States Patent
Smith et al.

(10) Patent No.: US 11,287,495 B2
(45) Date of Patent: Mar. 29, 2022

(54) METHODS AND APPARATUS FOR USE WITH COCHLEAR IMPLANTS HAVING MAGNET APPARATUS WITH MAGNETIC MATERIAL PARTICLES

(71) Applicant: ADVANCED BIONICS AG, Staefa (CH)

(72) Inventors: James George Elcoate Smith, Santa Clarita, CA (US); Sung Jin Lee, Valencia, CA (US); Jeryle L. Walter, Valencia, CA (US); Uli Gommel, Valencia, CA (US); Stephanie M. Reed, Conshohocken, PA (US)

(73) Assignee: Advanced Bionics AG, Staefa (CH)

( * ) Notice: Subject to any disclaimer, the term of this patent is extended or adjusted under 35 U.S.C. 154(b) by 258 days.

(21) Appl. No.: 16/610,502

(22) PCT Filed: May 22, 2017

(86) PCT No.: PCT/US2017/033757
§ 371 (c)(1),
(2) Date: Nov. 2, 2019

(87) PCT Pub. No.: WO2018/217187
PCT Pub. Date: Nov. 29, 2018

(65) Prior Publication Data
US 2021/0156934 A1     May 27, 2021

(51) Int. Cl.
*A61N 1/08*     (2006.01)
*G01R 33/28*    (2006.01)
*A61N 1/05*     (2006.01)

(52) U.S. Cl.
CPC ......... *G01R 33/285* (2013.01); *A61N 1/0541* (2013.01); *A61N 1/086* (2017.08); *G01R 33/288* (2013.01)

(58) Field of Classification Search
CPC ........ A61B 5/055; A61B 5/70; A61N 1/0541; A61N 1/086; G01R 33/285; G01R 33/288
See application file for complete search history.

(56) References Cited

U.S. PATENT DOCUMENTS

| 4,214,366 A | 7/1980 | Laban |
| 4,352,960 A | 10/1982 | Dormer et al. |

(Continued)

FOREIGN PATENT DOCUMENTS

| EP | 2117489 B1 | 5/2010 |
| EP | 2853287 A1 | 4/2015 |

(Continued)

OTHER PUBLICATIONS

U.S. Appl. No. 16/499,311, filed Sep. 29, 2019, 20210106815 A1.

(Continued)

*Primary Examiner* — George Manuel
(74) *Attorney, Agent, or Firm* — Henricks Slavin LLP (57) ABSTRACT

A particle alignment method in accordance with at least one of the present inventions includes the step of positioning a cochlear implant, which is implanted within a patient's head and which includes a magnet apparatus with a central axis and magnetic material particles, at a location outside of the scanning area of an MRI system, adjacent to the MRI system, and within the MRI magnetic field in such a manner that the central axis of the magnet apparatus is at least substantially parallel to the MRI magnetic field.

19 Claims, 9 Drawing Sheets

(56) References Cited

U.S. PATENT DOCUMENTS

| | | |
|---|---|---|
| 4,595,390 A | 6/1986 | Hakim et al. |
| 4,606,329 A | 8/1986 | Hough |
| 4,612,915 A | 9/1986 | Hough et al. |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,032,677 A | 3/2000 | Blechman et al. |
| 6,178,353 B1 | 1/2001 | Griffith et al. |
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,461,288 B1 | 10/2002 | Holcomb |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian et al. |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,027,735 B1 | 9/2011 | Tziviskos et al. |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 10,532,209 B2 | 1/2020 | Lee et al. |
| 10,646,712 B2 | 5/2020 | Smith et al. |
| 10,646,718 B2 | 5/2020 | Smith et al. |
| 10,806,936 B2 | 10/2020 | Crawford et al. |
| 10,821,279 B2 | 11/2020 | Lee et al. |
| 11,097,095 B2 | 8/2021 | Smith et al. |
| 2004/0012470 A1 | 1/2004 | Zimmerling et al. |
| 2004/0059423 A1 | 3/2004 | Barnes et al. |
| 2004/0063072 A1 | 4/2004 | Honkura et al. |
| 2004/0210103 A1 | 10/2004 | Westerkull |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0116743 A1 | 6/2006 | Gibson et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0097496 A1 | 4/2008 | Chang et al. |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0150657 A1 | 6/2013 | Leigh et al. |
| 2013/0184804 A1 | 7/2013 | Dalton |
| 2013/0281764 A1 | 10/2013 | Bjorn et al. |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0232382 A1* | 8/2014 | Goodyear ............... G01V 3/08 324/239 |
| 2014/0336447 A1 | 11/2014 | Bjorn et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0094521 A1 | 4/2015 | Neuman et al. |
| 2015/0100109 A1 | 4/2015 | Feldman et al. |
| 2015/0265842 A1 | 9/2015 | Ridler |
| 2015/0320523 A1 | 11/2015 | Way et al. |
| 2015/0367126 A1 | 12/2015 | Smyth |
| 2015/0382114 A1 | 12/2015 | Andersson et al. |
| 2016/0008596 A1 | 1/2016 | Gibson et al. |
| 2016/0023006 A1 | 1/2016 | Ridler et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0213936 A1 | 7/2016 | Heerlein et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2017/0347208 A1 | 11/2017 | Jurkiewicz |
| 2018/0028818 A1 | 2/2018 | Andersson et al. |
| 2018/0056084 A1 | 3/2018 | Alam |
| 2018/0110985 A1 | 4/2018 | Walter |
| 2018/0110986 A1 | 4/2018 | Lee |
| 2018/0133486 A1 | 5/2018 | Smith |
| 2018/0146308 A1 | 5/2018 | Leigh et al. |
| 2018/0160241 A1 | 6/2018 | Gustafsson et al. |
| 2018/0160242 A1 | 6/2018 | Sriskandarajah |
| 2018/0185634 A1 | 7/2018 | Smyth |
| 2018/0249262 A1 | 8/2018 | Santek |
| 2018/0270591 A1 | 9/2018 | Kennes |
| 2018/0296826 A1 | 10/2018 | Lee et al. |
| 2018/0303602 A1 | 10/2018 | Leigh |
| 2018/0304078 A1 | 10/2018 | Crawford et al. |
| 2018/0369586 A1 | 12/2018 | Lee et al. |

(56) References Cited

U.S. PATENT DOCUMENTS

| | | |
|---|---|---|
| 2019/0015662 A1 | 1/2019 | Raje et al. |
| 2019/0046797 A1 | 2/2019 | Calixto et al. |
| 2019/0053908 A1 | 2/2019 | Cook et al. |
| 2019/0076649 A1 | 3/2019 | Lee et al. |
| 2019/0255316 A1 | 8/2019 | Lee et al. |
| 2019/0298417 A1 | 10/2019 | Barrett et al. |
| 2020/0114151 A1 | 4/2020 | Smith et al. |
| 2020/0230422 A1 | 7/2020 | Gibson et al. |
| 2020/0238088 A1 | 7/2020 | Smith et al. |
| 2020/0330777 A1 | 10/2020 | Smith et al. |
| 2020/0391023 A1 | 12/2020 | Lee et al. |
| 2021/0046311 A1 | 2/2021 | Brehm et al. |
| 2021/0106815 A1 | 4/2021 | Smith et al. |
| 2021/0299456 A1 | 9/2021 | Smith et al. |
| 2021/0316136 A1 | 10/2021 | Smith et al. |
| 2021/0339021 A1 | 11/2021 | Brehm et al. |

FOREIGN PATENT DOCUMENTS

| | | |
|---|---|---|
| EP | 2560730 B1 | 11/2016 |
| EP | 3138605 A1 | 3/2017 |
| EP | 2098198 B1 | 9/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |
| WO | WO2017172566 A1 | 10/2017 |
| WO | WO2018190813 A1 | 10/2018 |
| WO | WO2018191314 A1 | 10/2018 |
| WO | WO2018199936 A1 | 11/2018 |
| WO | WO2018217187 A1 | 11/2018 |
| WO | WO2019083540 A1 | 5/2019 |
| WO | WO2019160555 A1 | 8/2019 |
| WO | WO2020092185 A1 | 5/2020 |
| WO | WO2021201845 A1 | 10/2021 |

OTHER PUBLICATIONS

U.S. Appl. No. 17/355,225, filed Jun. 23, 2021.
U.S. Appl. No. 17/335,161, filed Jun. 1, 2021.
U.S. Appl. No. 17/346,343, filed Jun. 14, 2021.
U.S. Appl. No. 16/499,311, filed Sep. 29, 2019.
U.S. Appl. No. 16/754,126, filed Apr. 6, 2020.
U.S. Appl. No. 16/966,885, filed Aug. 1, 2020.
PCT Invitation to Pay Additional Fees and Partial International Search dated Feb. 23, 2018 for PCT App. Ser. No. PCT/US2017/033757.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
U.S. Appl. No. 15/568,469, filed Oct. 21, 2017, 20180110985 A1.
U.S. Appl. No. 15/770,207, filed Apr. 22, 2018, U.S. Pat. No. 10,806,936.
U.S. Appl. No. 17/073,322, filed Oct. 17, 2020, 20210170167 A1.
U.S. Appl. No. 16/060,383, filed Jun. 7, 2018, U.S. Pat. No. 10,532,209.
U.S. Appl. No. 15/591,054, filed May 9, 2017, U.S. Pat. No. 9,919,154.
U.S. Appl. No. 16/009,600, filed Jun. 15, 2018, U.S. Pat. No. 10,821,279.
U.S. Appl. No. 16/403,582, filed May 5, 2019, U.S. Pat. No. 10,463,849.
U.S. Appl. No. 17/008,291, filed Aug. 31, 2020, 20200391023 A1.
U.S. Appl. No. 16/610,502, filed Nov. 2, 2019, 20210156934 A1.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, U.S. Pat. No. 10,646,712.
U.S. Appl. No. 15/805,025, filed Nov. 6, 2017, U.S. Pat. No. 10,646,718.
U.S. Appl. No. 16/852,457, filed Apr. 18, 2020, 20200238088 A1.
U.S. Appl. No. 16/499,311, filed Sep. 29, 2019, U.S. Pat. No. 11,097,095.
U.S. Appl. No. 17/355,225, filed Jun. 23, 2021, 20210316136 A1.
U.S. Appl. No. 16/603,868, filed Oct. 9, 2019, 20200114151 A1.
U.S. Appl. No. 16/754,126, filed Apr. 6, 2020, 20200330777 A1.
U.S. Appl. No. 17/335,161, filed Jun. 1, 2021, 20210339021 A1.
U.S. Appl. No. 17/346,343, filed Jun. 14, 2021, 20210299456 A1.
U.S. Appl. No. 17/499,813, filed Oct. 12, 2021.

* cited by examiner

METHODS AND APPARATUS FOR USE WITH COCHLEAR IMPLANTS HAVING MAGNET APPARATUS WITH MAGNETIC MATERIAL PARTICLES

CROSS-REFERENCE TO RELATED APPLICATIONS

This application is the U.S. National Stage of PCT App. Ser. No. PCT/US2017/033757, filed May 22, 2017.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 10 mm thick.

The magnitude of the retention force between the headpiece magnet and implant magnet is an important aspect of an ICS system. If the force is too low, the headpiece will not remain in place on the head during typical activities. If, on the other hand, the force is too high, the pressure on the skin flap can result is discomfort and tissue necrosis. The magnitude of the retention force is dictated by the strength of the magnets and the distance between the magnets, which is a function of the thickness of the skin flap. The strength of the headpiece magnet is frequently selected during the post-implantation headpiece fitting processes.

Figure 1:
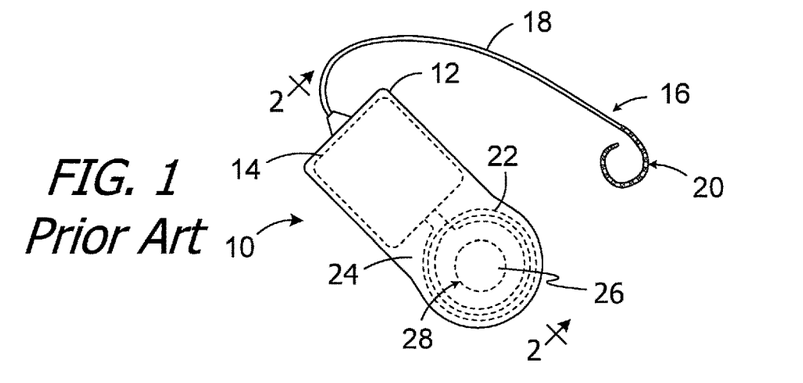
FIG. 1 is a plan view of a conventional cochlear implant.
Figure 2:
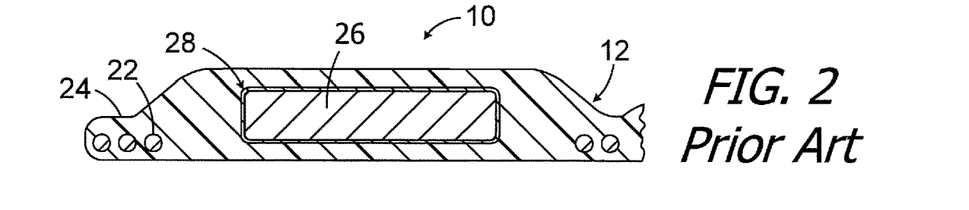
FIG. 2 is a section view taken along line 2-2 in FIG. 1.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material (e.g., with a hardness from 50 to 70 Shore A), a processor assembly 14, a cochlear lead 16 with a flexible body 18 and an electrode array 20, and an antenna 22 that may be used to receive data and power by way of an external antenna that is associated with, for example, a sound processor unit. The antenna 22 is located within an antenna portion 24 of the housing 12. A cylindrical positioning magnet 26, with north and south magnetic dipoles that are aligned in the axial direction of the disk, is located within the housing magnet pocket 28. The positioning magnet 26 is used to maintain the position of a headpiece transmitter over the antenna 22.

Figure 3:
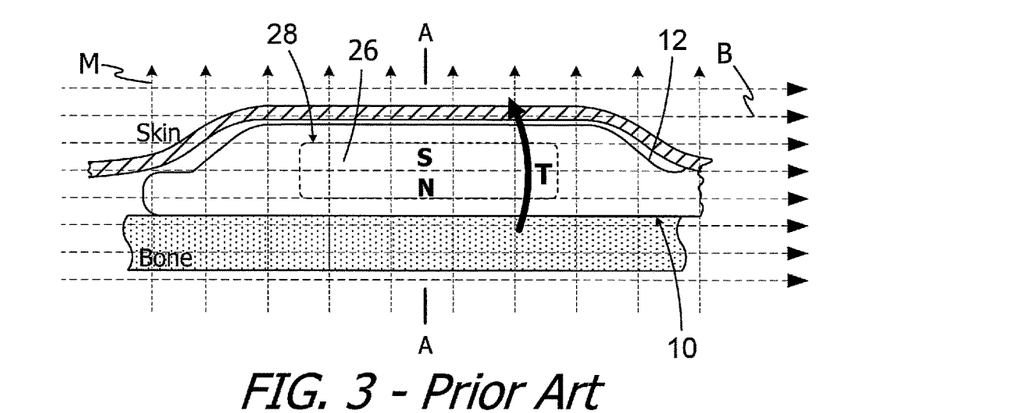
FIG. 3 is a partial section view showing the conventional cochlear implant as an MRI magnetic field is being applied.

Some conventional cochlear implants are not compatible with magnetic resonance imaging ("MRI") systems. As illustrated in FIG. 3, the implant positioning magnet 26 produces a magnetic field M in a direction that is perpendicular to the patient's skin and parallel to the central axis A. This magnetic field direction is not aligned with, and may be perpendicular to (as shown), the direction of the MRI magnetic field B when the patient is within the MRI system. The misalignment of the interacting magnetic fields M and B is problematic for a number of reasons. The dominant MRI magnetic field B (typically 1.5 Tesla or more) may generate a significant amount of torque T on the implant magnet 26. The torque T may be sufficient to deform the housing 12 and cause reorientation of the implant magnet. Reorientation of the magnet 26 can place significant stress on the dermis (or "skin"), which cause significant pain. In some instances, the implant magnet 26 may rotate 180 degrees, thereby reversing the N—S orientation of the magnet.

One proposed solution to the problems associated with MRI magnetic fields is to provide cochlear implants with a magnet aperture that allows the magnet to be removed from the cochlear implant, and then reinserted into the cochlear implant, in situ, i.e., with the cochlear implant accessed by way of an incision in the skin. The present inventors haves determined that removal and reinsertion can be problematic because some patients will have many MRI procedures during their lifetimes, and repeated surgeries can result in skin necrosis at the implant site.

More recently, magnet apparatus that are compatible with MRI systems have been developed for use in cochlear implants. Various examples of an MRI-compatible magnet apparatus are disclosed in WO2016/190886 and WO2016/191429, which are incorporated herein by reference in their entireties. The magnet apparatus 30 illustrated in FIGS. 4 and 5, which may be incorporated into the cochlear implant 10 in place of the magnet 26, includes a case 32, with base 34 and a cover 36, and magnetic material particles (or "particles") 38 within the internal volume of the case 32.

Figure 4:
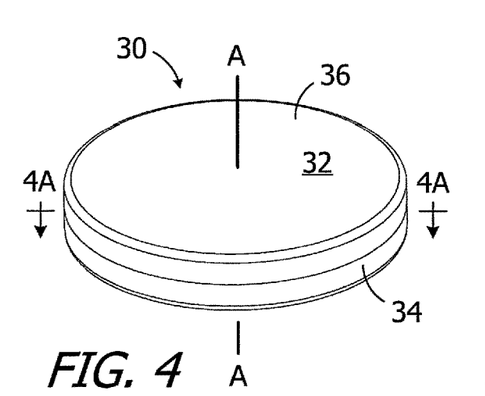
FIG. 4 is a perspective view of a particle-based MRI-compatible magnet apparatus.
Figure 5:
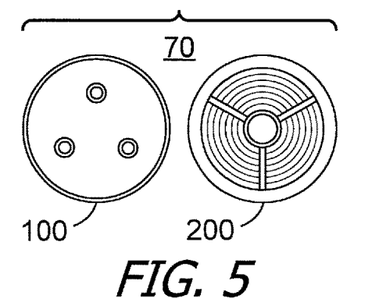
FIG. 5 is a top view of a particle alignment indication kit in accordance with one embodiment of a present invention.

The particles 38 are independently and freely rotatable and otherwise movable relative to one another and to the case 32, and are free to move from one X-Y-Z coordinate to another and/or rotate in any direction. For example, some particles 38 may move linearly and/or rotate relative to other particles and relative to the case 32, while the orientation of the case remains the same, when the magnet apparatus 30 is exposed to an external magnetic field. Although not limited to any particular shape, the magnetic material particles 38 may be spherical or may be non-spherical, polyhedral shapes or at least substantially polyhedral shapes, i.e., multi-sided shapes that are regular or irregular, symmetric or asymmetric, with or without smooth side surfaces, and with or without straight edges, that will permit the particles to rotate relative to one another when loosely packed. Any three-dimensional shapes that permit the movement described above may also be employed. The magnetic material particles 38 may be formed from materials that include, but are not limited to, neodymium-iron-boron ("$Nd_2Fe_{14}B$") magnetic material, isotropic neodymium, anisotropic neodymium, samarium-cobalt ("$Sm_2Co_{17}$"). An external magnetic field may be used to reorient the magnetic material particles 38 within the case 32 such that the N—S orientations of the particles are the same (i.e., the particles are "aligned"). For example, the magnet apparatus 30 may be positioned adjacent to a magnet (e.g., a rare-earth magnet) that creates a magnetic field of 1.5 Tesla or more to reorient the magnetic material particles 38. This alignment establishes the desired N—S orientation of the magnet apparatuses 30 (e.g., parallel to the central axis A). Such reorientation may be performed before or after the magnet apparatus 30 is incorporated into a cochlear implant and prior to the implant being implanted into the patient.

Although magnetic material particle-based MRI-compatible magnet apparatus are an advance in the art, the present inventors have determined that the magnetic material particles may become misaligned (i.e., no longer aligned with one another and/or in their desired N—S orientation) subsequent to being exposed to a relatively strong MRI magnetic field B (e.g., 3.0 Tesla or more). The misalignment reduces the attraction strength of the magnet apparatus and, accordingly, impairs the ability of the magnet apparatus to maintain the position of a headpiece transmitter over the cochlear implant antenna.

SUMMARY

A particle alignment method in accordance with at least one of the present inventions includes the step of positioning a cochlear implant, which is implanted within a patient's head and which includes a magnet apparatus with a central axis and magnetic material particles, at a location outside of the scanning area of an MRI system, adjacent to the MRI system, and within the MRI magnetic field in such a manner that the central axis of the magnet apparatus is at least substantially parallel to the MRI magnetic field.

A particle alignment indication kit in accordance with at least one of the present inventions includes a location identification template including a template magnet and at least one aperture and an alignment gauge including a gauge magnet and an at least substantially transparent member associated with the gauge magnet.

A method in accordance with at least one of the present inventions includes the steps of, prior to an MRI procedure where the patient is placed into a scanning area of an MRI system that includes an MRI magnet that creates an MRI magnetic field, placing a location identification template on the patient's head and over the magnet apparatus of an implanted cochlear implant and making at least one mark on the patient's head based on the position of the location identification template, removing the location identification template from the patient's head after the at least one mark has been made and prior to the MRI procedure, and after the MRI procedure, placing an alignment gauge on the patient's head and over the magnet apparatus and determining whether or not the magnetic material particles of the magnet apparatus are in the pre-MRI orientation by observing the position of the at least one mark on the patient's head relative to the alignment gauge.

There are a number of advantages associated with such apparatus and methods. By way of example, but not limitation, at least some of the present inventions may be used to determine whether or not the magnetic material particles in an MRI-compatible magnet apparatus are in their desired N—S orientation. At least some of the present inventions may be used to return magnetic material particles in an MRI-compatible magnet apparatus to their desired N—S orientation after an MRI procedure has been performed.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

As illustrated in FIG. 5, one example of a particle alignment indication kit 70 includes a location identification template 100, which is discussed in greater detail below with reference to FIGS. 6 and 7, and an alignment gauge 200, which is discussed in greater detail below with reference to FIGS. 8-11. The particle alignment indication kit 70 may be used, for example, in the manner described below with reference to FIGS. 12-17 to determine whether or not exposure to a relatively strong MRI magnetic field has caused the magnetic material particles in a magnetic material particle-based MRI-compatible magnet apparatus to become misaligned.

Figure 6:
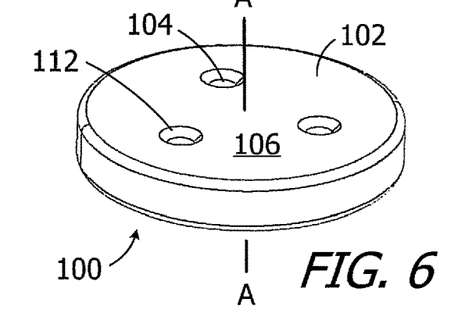
FIG. 6 is a perspective view of a location identification template in accordance with one embodiment of a present invention.
Figure 7:
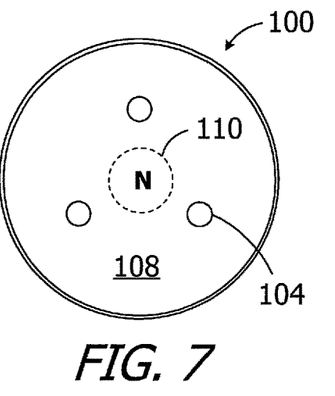
FIG. 7 is a bottom view of the location identification template illustrated in FIG. 6.
Figure 8:
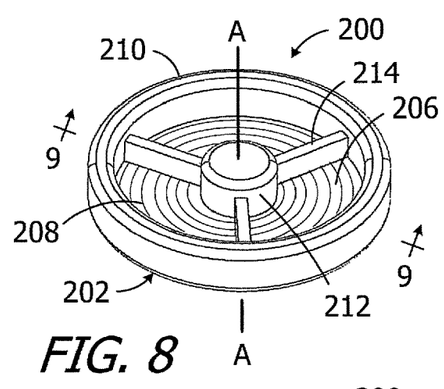
FIG. 8 is a perspective view of an alignment gauge in accordance with one embodiment of a present invention.
Figure 9:
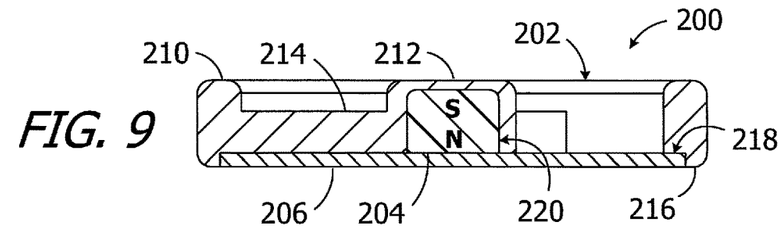
FIG. 9 is a section view take along line 9-9 in FIG. 8.
Figure 10:
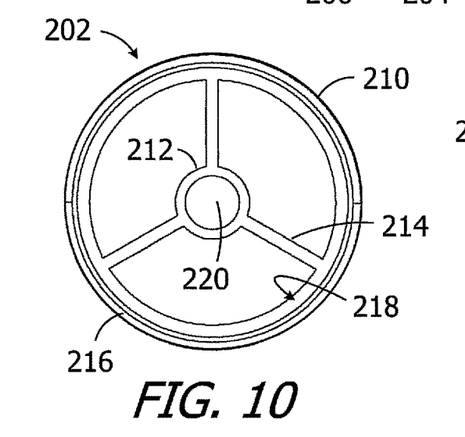
FIG. 10 is a bottom view of a portion of the alignment gauge illustrated in FIG. 8.
Figure 11:
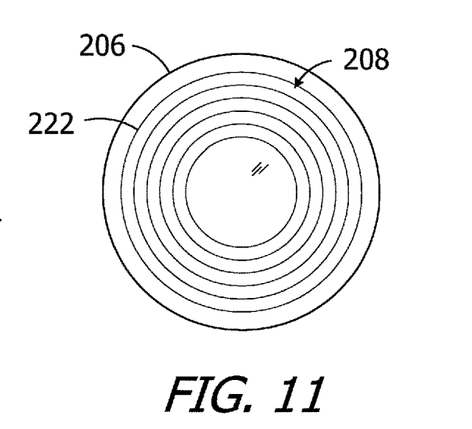
FIG. 11 is a top view of a portion of the alignment gauge illustrated in FIG. 8.

Turning to FIGS. 6 and 7, the exemplary location identification template 100 includes a disc-shaped housing 102 with a plurality of apertures 104 that extend from the top surface 106 of the template (i.e., the surface that faces away from the skin) to the bottom surface 108 of the template (i.e., the surface that faces the skin). A magnet 110 is located within the housing 102 with N pole facing the bottom surface 108. The apertures are equidistant from the central axis A of the template 100. The magnet 110 may be a cylindrical magnet similar to the magnets typically found in the headpieces of cochlear implant systems. During use, the tip of a pen or other biocompatible skin marking instrumentality may be inserted through the apertures 104. To that end, the apertures 104 include a funnel 112 at the top surface 106 to facilitate entry of the skin marking instrumentality into the apertures.

In other implementations, the location identification template (not shown) may simply be in the form of a magnet having a size and shape similar to housing 102 as well as the apertures 104.

The exemplary alignment gauge 200 illustrated in FIGS. 8-11 includes a frame 202, a magnet 204 that is carried by the frame, and a transparent (or at least substantially transparent) disc or other member 206 with a reticle or other indicia 208. As used herein, an "at least substantially transparent" disc or other member is a disc or other member that, although not perfectly transparent, allow a person to observe location marks M (discussed below) through the disc or other member. The exemplary frame 202 includes an outer ring 210, a magnet carrier 212, and a plurality of spokes 214 that mount the magnet carrier to the outer ring. The bottom surface 216 of the outer ring 210 includes an indentation 218 to accommodate the transparent disc 206, while the magnet carrier 212 includes a recess 220 for the magnet 204. The magnet 204, which may be similar to the magnets typically found in the headpieces of cochlear implant systems, is oriented such that the N pole faces the disc 206. The reticle 208 in the exemplary implementation includes a plurality of circles 222 that extend around the magnet carrier 212. The frame 202, a magnet 204, and circles 222 are concentric and share common axis A. Alpha-numeric indicia, such as circle numbering, may be added to the reticle 208 in some implementations.

In other implementations, the alignment gauge (not shown) may simply include a magnet 204 directed secured to a disc 206 with a reticle or other indicia 208.

Figure 4A:
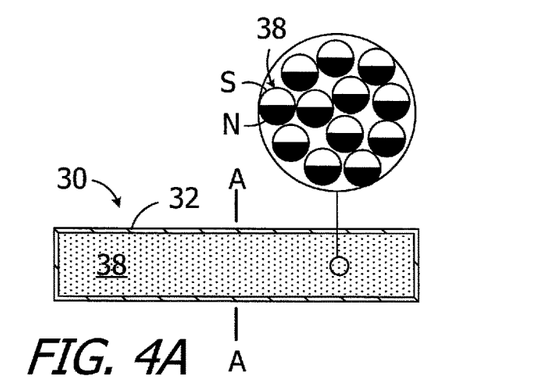
FIG. 4A is a section view take along line 4A-4A in FIG. 4.
Figure 12:
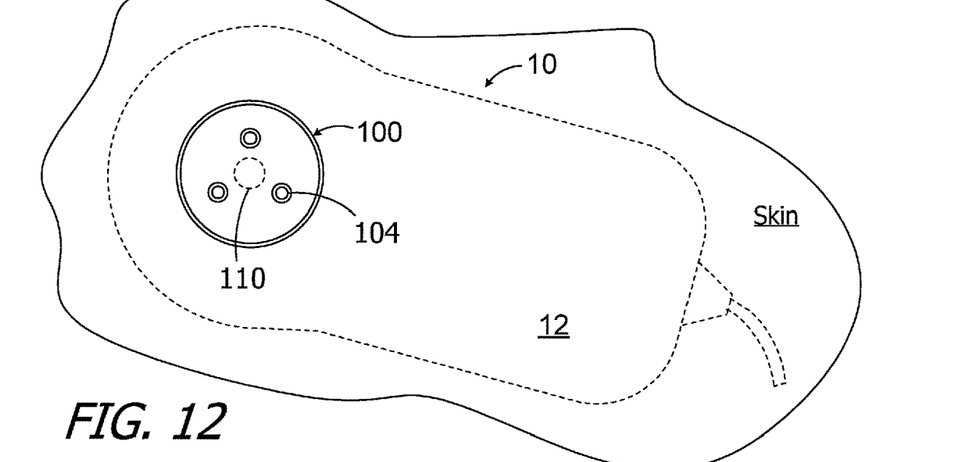
FIG. 12 is an elevation view showing the location identification template illustrated in FIG. 6 positioned over an implanted cochlear implant.
Figure 13:
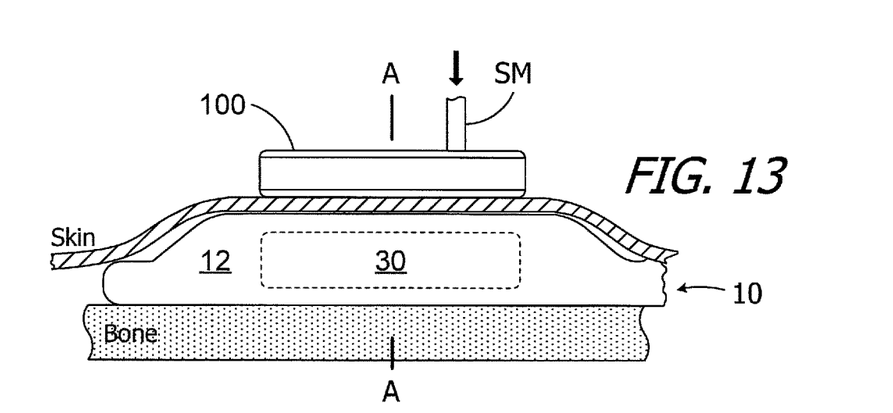
FIG. 13 is a partial section view showing the location identification template illustrated in FIG. 6 positioned over the implanted cochlear implant.
Figure 14:
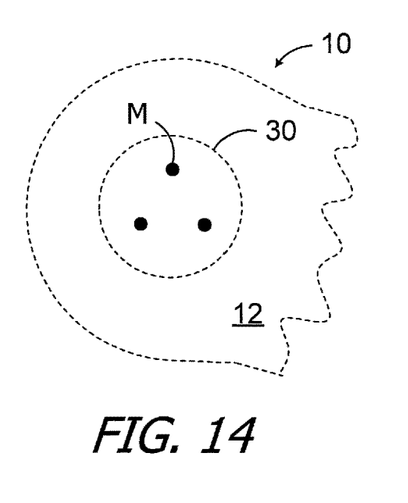
FIG. 14 is an elevation view showing location identification template markings over the implanted cochlear implant magnet apparatus.
Figure 15:
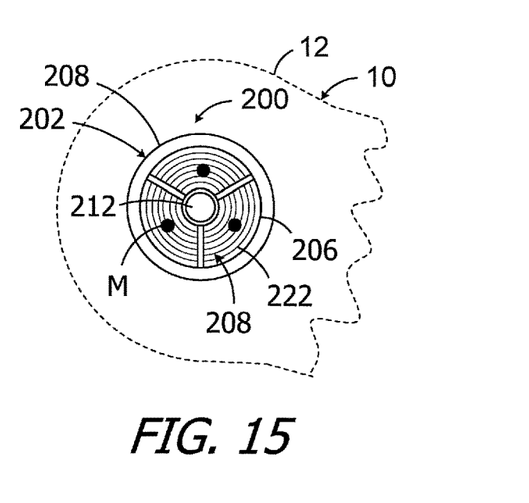
FIG. 15 is an elevation view showing the alignment gauge illustrated in FIG. 8 in an aligned state over the template markings and implanted cochlear implant magnet apparatus.

The exemplary particle alignment indication kit 70 may be employed in the manner illustrated in FIGS. 12-17. Prior to an MRI procedure, the location identification template 100 may be used to identify the center of an implanted magnet apparatus (e.g., magnet apparatus 30). The location identification template 100 may be placed on the patient's head over the cochlear implant 10 and, in particular, over the particle-based magnet apparatus 30 (FIGS. 12-13). The magnetic attraction between the location identification template 100 and the magnet apparatus 30 will be sufficient to hold the location identification template in place on the patient's head. Put another way, the magnet 110 performs the function of affixing the location identification template 100 on the patient's head through magnetic attraction with the implanted magnet apparatus 30. The particles 38 (FIG. 4A) will be aligned with one another prior to the MRI-procedure and, accordingly, the location identification template 100 will align itself with the magnet apparatus 30. In other words, the location identification template 100 and the magnet apparatus 30 will be coaxial, and the center of the location identification template will be aligned with center of the magnet apparatus. As such, the apertures 104 will be equidistant from the central axis (and center) of the magnet apparatus 30.

A pen or other biocompatible skin marking instrumentality SM may then be inserted through the each of the apertures 104 to create location marks M (FIG. 14) on the patient's skin. Like the apertures 104, the location marks M are equidistant from the central axis (and center) of the magnet apparatus 30.

The exemplary alignment gauge 200 may be positioned over the magnet apparatus 30 after the MRI procedure, or after the post-MRI realignment procedure discussed below with reference to FIGS. 29-34, to determine whether or not the magnetic material particles of the magnet apparatus 30 are in their pre-MRI procedure N—S orientations. The magnetic attraction between the alignment gauge 200 and the magnet apparatus 30 will be sufficient to hold the alignment gauge in place on the patient's head. Put another way, the magnet 204 performs the function of affixing the alignment gauge 200 on the patient's head through magnetic attraction with the implanted magnet apparatus 30. In those instances where the magnetic material particles are in their pre-MRI procedure N—S orientations (FIG. 15), the magnet 204 (FIG. 9) within the magnet carrier 212 will be coaxial with and centered relative to the magnet apparatus 30. As a result, the alignment gauge 200 will be coaxial with and centered relative to the magnet apparatus 30 and, accordingly, the location marks M on the patient's skin. The location marks M are also visible through the transparent disc 206, which allows the clinician to observe the location marks relative to the reticle 208. When the alignment gauge 200 is coaxial with and centered relative to the magnet apparatus 30, the location marks M will all be aligned with the same reticle circle 222 (or circles 222 if there is overlap). In the illustrated implementation, the third reticle circle 222 from the center passes through each location mark M.

Figure 16:
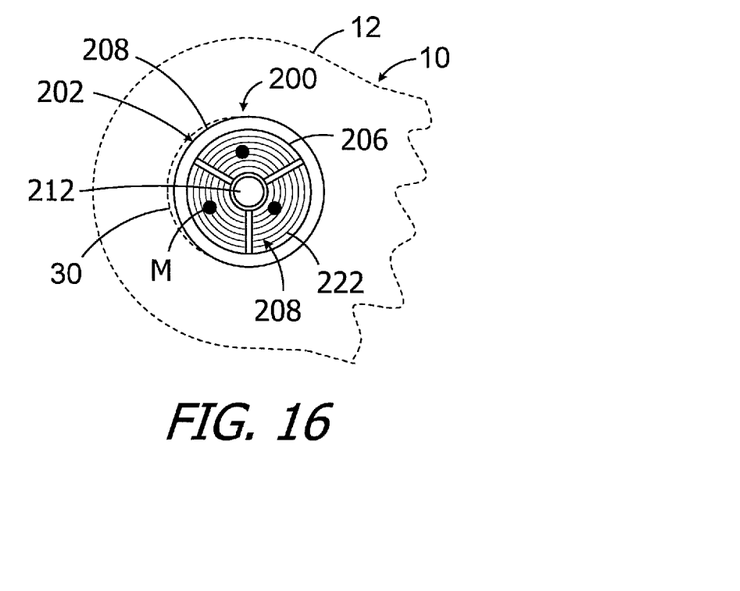
FIG. 16 is an elevation view showing the alignment gauge illustrated in FIG. 8 in a misaligned state over the template markings and implanted cochlear implant magnet apparatus.
Figure 17:
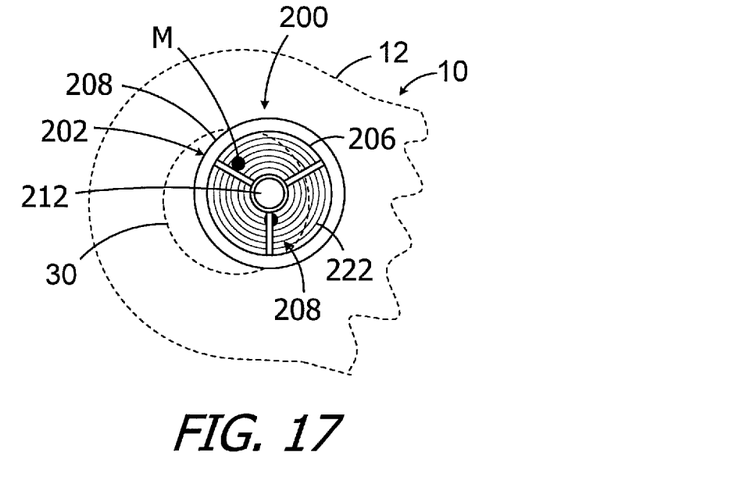
FIG. 17 is an elevation view showing the alignment gauge illustrated in FIG. 8 in a misaligned state over the template markings and implanted cochlear implant magnet apparatus.

As illustrated in FIG. 16, when the magnetic material particles of the magnet apparatus 30 are slightly misaligned, as compared to their pre-MRI procedure N—S orientations, the exemplary alignment gauge 200 will be slightly misaligned relative to the magnet apparatus. The position of the location marks M relative to the reticle 208 is indicative of the misalignment as well as the magnitude thereof. Here, two of the location marks M are aligned with the fourth reticle circle 222 from the center, and one of the location marks M is aligned with the second reticle circle 222 from the center. Turning to FIG. 17, which illustrates an instance where the magnetic material particles of the magnet apparatus 30 are substantially misaligned, as compared to their pre-MRI procedure N—S orientations, the exemplary alignment gauge 200 will be substantially misaligned relative to the magnet apparatus. Two of the location marks M are completely or partially obscured by the frame 202, and one is adjacent to one of the frame spokes. In those instances where the particle alignment indication kit 70 shows that the post-MRI alignment of the particles of the magnet apparatus 30 (or other particle-based magnet apparatus) are misaligned, a realignment procedure such as that described below with reference to FIGS. 29-34 may be employed.

Figure 18:
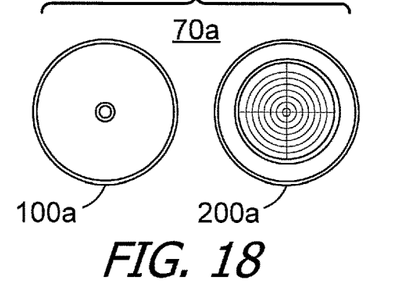
FIG. 18 is a top view of a particle alignment indication kit in accordance with one embodiment of a present invention.

Another exemplary particle alignment indication kit is generally represented by reference numeral 70a in FIG. 18. The particle alignment indication kit 70a is substantially similar to kit 70 and similar elements are represented by similar reference numerals. To that end, the particle alignment indication kit 70a includes a location identification template 100a, which is discussed in greater detail below with reference to FIGS. 19 and 20, and an alignment gauge 200a, which is discussed in greater detail below with reference to FIGS. 21-24. The particle alignment indication kit 70a may be used, for example, in the manner described below with reference to FIGS. 25-28 to determine whether or not exposure to a relatively strong MRI magnetic field has caused the magnetic material particles in a magnetic material particle-based MRI-compatible magnet apparatus to become misaligned.

Figure 19:
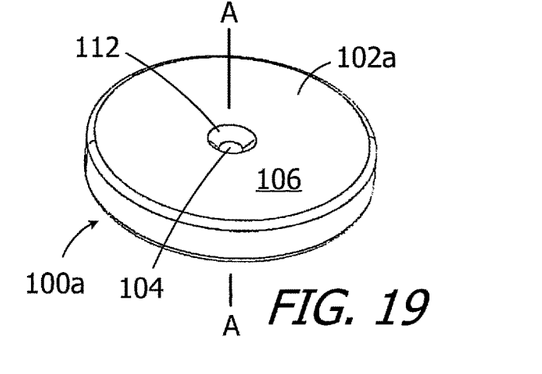
FIG. 19 is a perspective view of a location identification template in accordance with one embodiment of a present invention.
Figure 20:
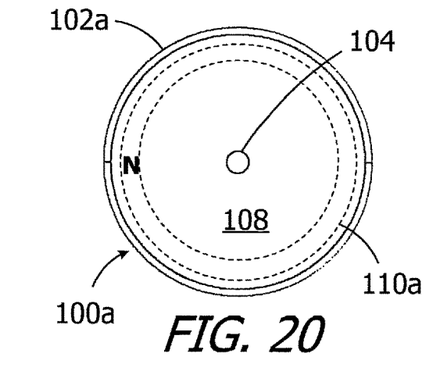
FIG. 20 is a bottom view of the location identification template illustrated in FIG. 19.
Figure 21:
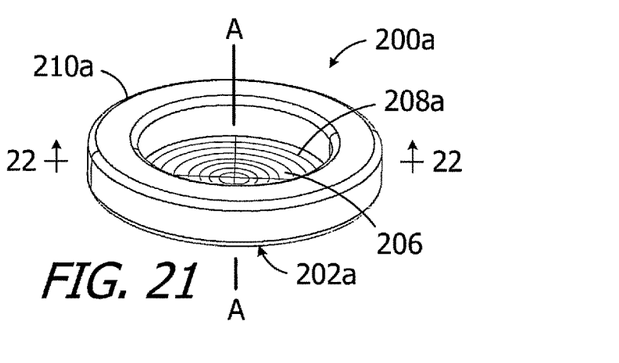
FIG. 21 is a perspective view of an alignment gauge in accordance with one embodiment of a present invention.
Figure 22:
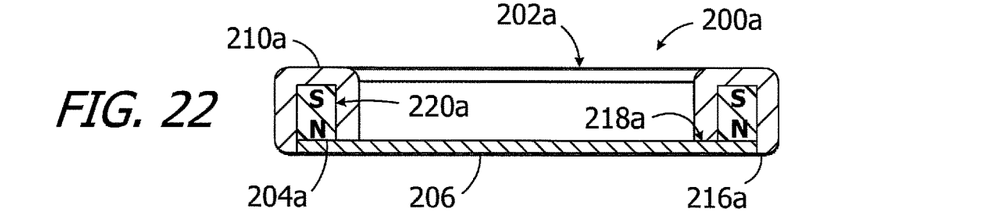
FIG. 22 is a section view take along line 22-22 in FIG. 21.
Figure 23:
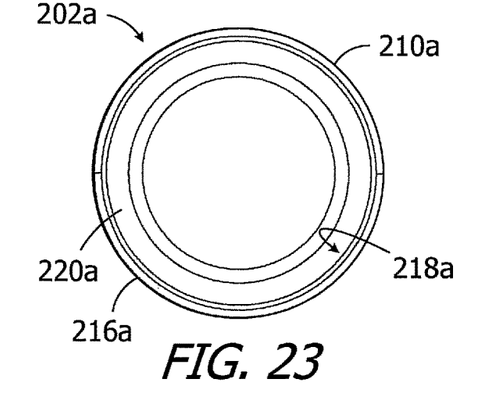
FIG. 23 is a bottom view of a portion of the alignment gauge illustrated in FIG. 21.
Figure 24:
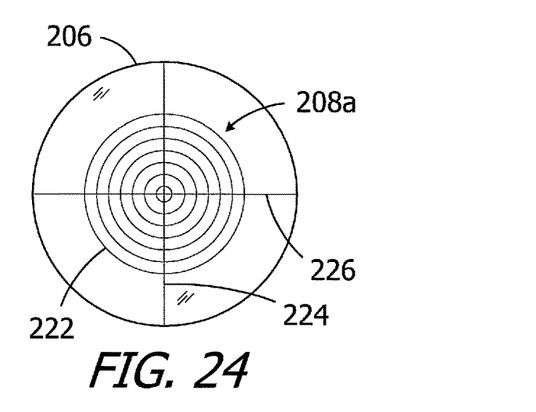
FIG. 24 is a top view of a portion of the alignment gauge illustrated in FIG. 21.

The exemplary location identification template 100a illustrated in FIGS. 19 and 20 includes a single aperture 104 (with a funnel 112) that extends from the top surface 106 of the template to the bottom surface 108 of the template housing 102a. The aperture 104 is located on the central axis A of the template 100a. An annular magnet 110a is located within the housing 102a with N pole facing the bottom surface 108.

In other implementations, the location identification template (not shown) may simply be in the form of a magnet having a size and shape similar to housing 102a as well as the single aperture 104.

Turning to FIGS. 21-24, the exemplary alignment gauge 200a includes an annular frame 202a, an annular magnet 204a that is carried by the frame, and a transparent (or at least substantially transparent) disc 206 with a reticle or other indicia 208a. The exemplary frame 202a includes a ring 210a having a bottom surface 216a with an indentation 218a to accommodate the transparent disc 206 and an annular recess 220a for the magnet 204a, which is oriented such that the N pole faces the disc 206. The reticle 208a includes a plurality of circles 222 as well as cross-hair with perpendicular lines 224 and 226. The frame 202a, a magnet 204a, and circles 222 are concentric and share a common axis A, and the center of the cross-hair is located on the common axis A.

Figure 25:
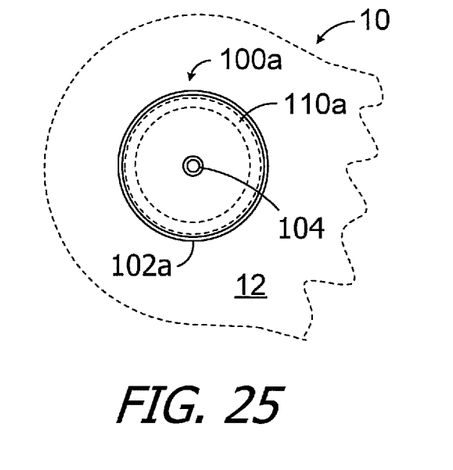
FIG. 25 is an elevation view showing the location identification template illustrated in FIG. 19 positioned over an implanted cochlear implant.
Figure 26:
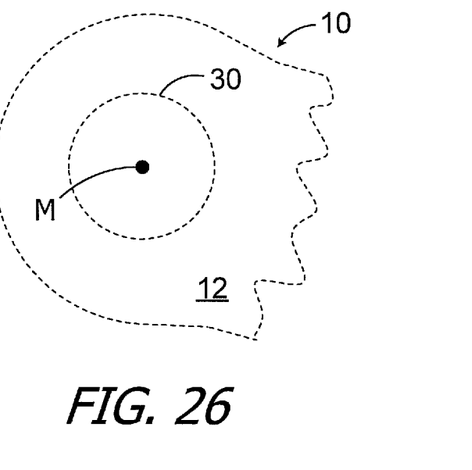
FIG. 26 is an elevation view showing a location identification template marking over the implanted cochlear implant magnet apparatus.
Figure 27:
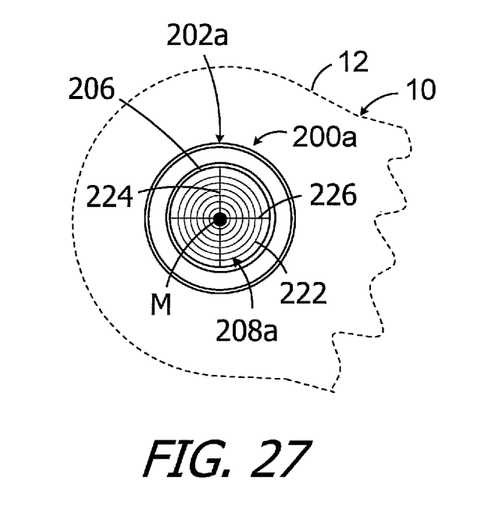
FIG. 27 is an elevation view showing the alignment gauge illustrated in FIG. 21 in an aligned state over the template marking and implanted cochlear implant magnet apparatus.
Figure 28:
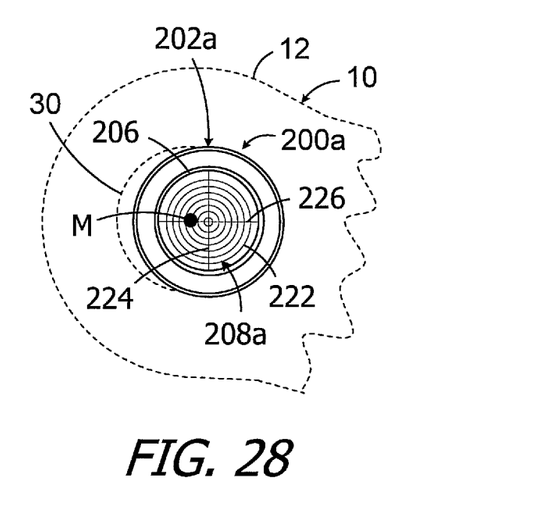
FIG. 28 is an elevation view showing the alignment gauge illustrated in FIG. 21 in a misaligned state over the template marking and implanted cochlear implant magnet apparatus.

The exemplary particle alignment indication kit 70a may be employed in a manner similar to the kit 70. Prior to an MRI procedure, the location identification template 100a may be placed on the patient's head over the cochlear implant 10 and, in particular, over the particle-based magnet apparatus 30 (FIG. 25). The particles 38 (FIG. 4A) will be aligned with one another prior to the MRI-procedure and, accordingly, the location identification template 100a will be attracted to, and will align itself with, the magnet apparatus 30 in the manner described above. A pen or other biocompatible skin marking instrumentality may then be inserted through the aperture 104 to create a location mark M (FIG. 26) on the patient's skin that is on the central axis (and center) of the magnet apparatus 30.

After the MRI procedure or post-MRI realignment procedure, the exemplary alignment gauge 200a may be positioned over the magnet apparatus 30. In those instances where the magnetic material particles of the magnet apparatus 30 are in their pre-MRI procedure N—S orientations (FIG. 27), the magnet 204a (FIG. 22) within the ring 210a will be coaxial with and centered relative to the magnet apparatus 30, as will the remainder of the alignment gauge 200a. The location mark M on the patient's skin will be visible through the transparent disc 206, which allows the clinician to observe the location marks relative to the reticle 208a. When the alignment gauge 200a is coaxial with and centered relative to the magnet apparatus 30, the location mark M will be located within the innermost reticle circle 222 at the intersection of the crosshair lines 224 and 226. Alternatively, when the magnetic material particles of the magnet apparatus 30 are misaligned as compared to their pre-MRI procedure N—S orientations, the exemplary alignment gauge 200a will be misaligned relative to the magnet apparatus and the position of the location mark M relative to the reticle 208a is indicative of the misalignment as well as the magnitude thereof.

With respect to materials and dimensions, suitable materials for the location identification template housings 102 and 102a, as well as the alignment gauge frames 202 and 202a, include but are not limited to, biocompatible thermoplastics such as acrylonitrile butadiene styrene (ABS), nylon and polyoxymethylene (POM). The outer diameter of the exemplary housings 102 and 102a and frames 202 and 202a may be similar to that of a cochlear implant headpiece, i.e., between about 12 mm and 28 mm.

A conventional MRI system may be employed in the present methods to reorient the magnetic material particles within a cochlear implant magnet apparatus (e.g., magnet apparatus 30) into their pre-MRI procedure N-S orientations. To that end, it should be noted here that an MRI procedure will not demagnetize the magnetic material particles (e.g., particles 38) in a magnetic material particle-based MRI-compatible magnet apparatus (e.g., magnet apparatus 30) because the particles are free to orient themselves into alignment with the MRI magnetic field. Similarly, the reorientation of the magnetic material particles into their pre-MRI procedure N-S orientations is not a remagnetization of the particles.

Figure 29:
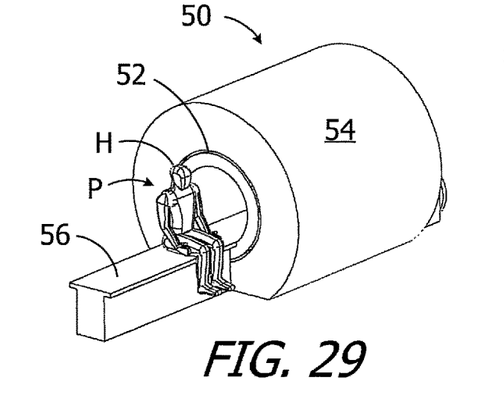
FIG. 29 is a perspective view of a method step in accordance with one embodiment of a present invention.
Figure 30:
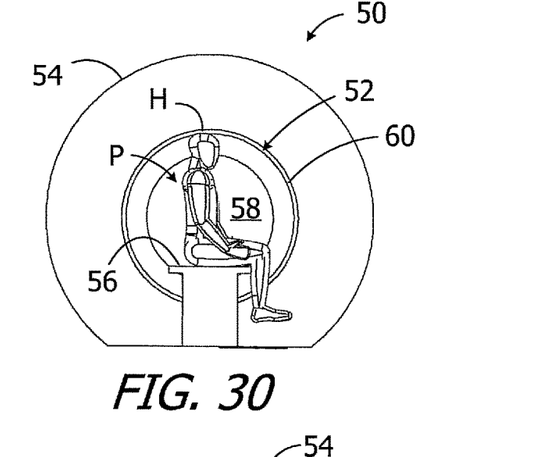
FIG. 30 is an end view of the method step illustrated in FIG. 29.
Figure 31:
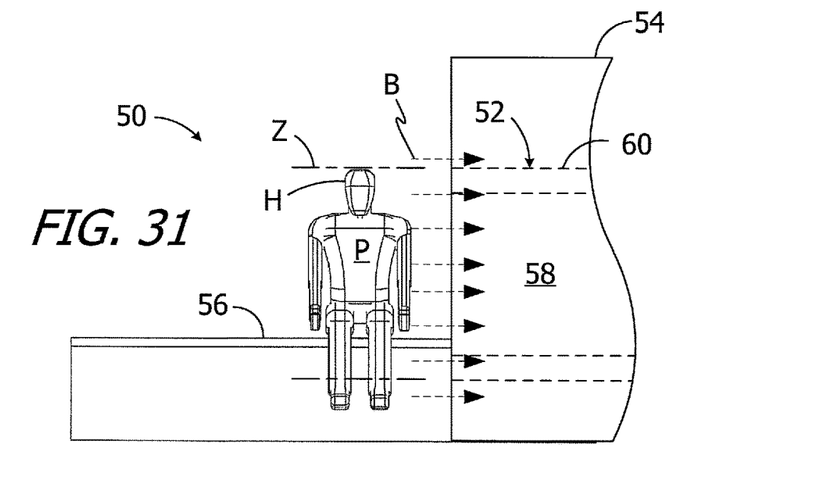
FIG. 31 is a front view of the method step illustrated in FIG. 29.

One example of a conventional MRI system is the MRI system 50 illustrated in FIGS. 29-31. The MRI system 50 includes, among other things, a cylindrical (or "closed bore") magnet 52 (or "MRI core"), an outer housing 54, and patient table 56 that allows the patient P to be moved into the scanning area 58 when the patient is in a prone position.

Figure 32:
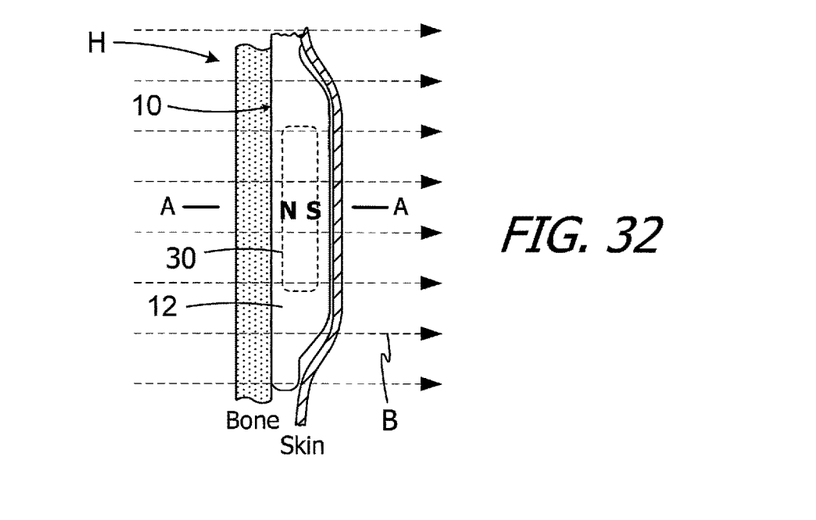
FIG. 32 is a partial section view of the method step illustrated in FIG. 29.

In one implementation of the present particle reorientation method, the patient P may be positioned adjacent to the longitudinal end of the MRI magnet 52 without the external cochlear implant sound processor and headpiece. For example, the patient P may be seated on the patient table 56. The patient's head H should be oriented in such a manner that the cochlear implant 10 is perpendicular to the direction of the MRI magnetic field B in the area closely adjacent to (e.g., 15 cm to 25 cm) the longitudinal end of the magnet 52. In some instances, the patient's shoulder may be located at the longitudinal end of the MRI magnet 52 (or scanning area 58). The patient's head H may also be located within a cylindrical zone Z which has an outer perimeter that is the same diameter as, and is aligned with, the outer perimeter 60 of the MRI magnet 52, as this is where the strength of the MRI magnetic field B is highest. With the head H located and oriented in this manner, the axis A of the magnet apparatus 30 is parallel to, or at least substantially parallel to, the MRI magnetic field B in the area closely adjacent to the longitudinal end of the magnet 52. As used herein, the phrase "at least substantially parallel" means "parallel±10°." The MRI magnetic field B will reorient the magnetic material particles 38 to their original N—S orientations (FIG. 4A), or within 5°, thereby returning the magnet apparatus 30 to the original N—S orientation as is illustrated in FIG. 32, or within 5° of the original N—S orientation. Although the MRI magnetic field B will typically reorient the magnetic material particles 38 almost instantaneously, the patient P may be kept in the illustrated location for about 10-15 minutes in order to, for example, counter any head movements and insure that proper alignment is achieved.

Figure 33:
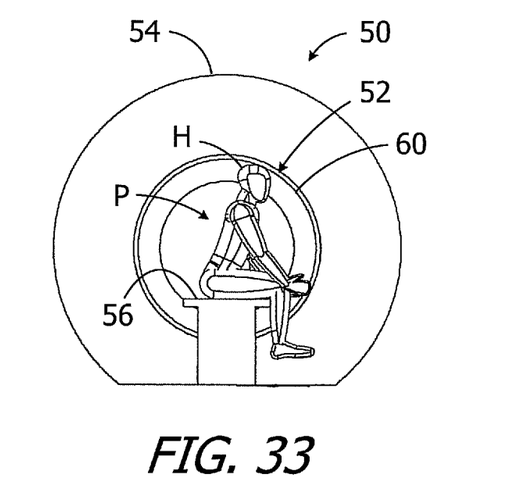
FIG. 33 is an end view of a method step in accordance with one embodiment of a present invention.
Figure 34:
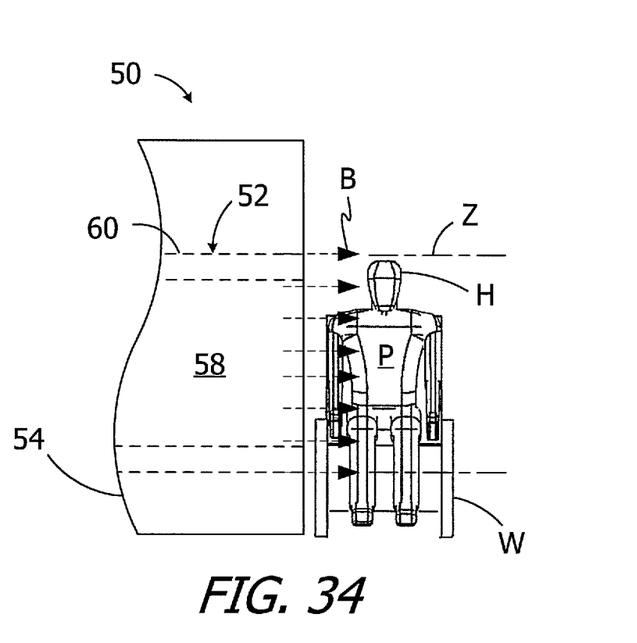
FIG. 34 is a front view of a method step in accordance with one embodiment of a present invention.

It should be noted that the present methods may be performed with the patient P positions and locations other than that illustrated in FIGS. 29-32. Referring for example to FIG. 33, the patient P may be allowed to lean forward. Here too, the patient's head H may be closely adjacent to the longitudinal end of the magnet 52, oriented in such a manner that the cochlear implant is perpendicular to the direction of the MRI magnetic field B, and located within the outer perimeter 60. As illustrated for example FIG. 34, a patient P in a wheelchair W may be positioned at the opposite end of the MRI system 50. Here again, the patient's head H may be closely adjacent to a longitudinal end of the magnet 52, oriented in such a manner that the cochlear implant is perpendicular to the direction of the MRI magnetic field B, and located within the outer perimeter 60.

Figure 35:
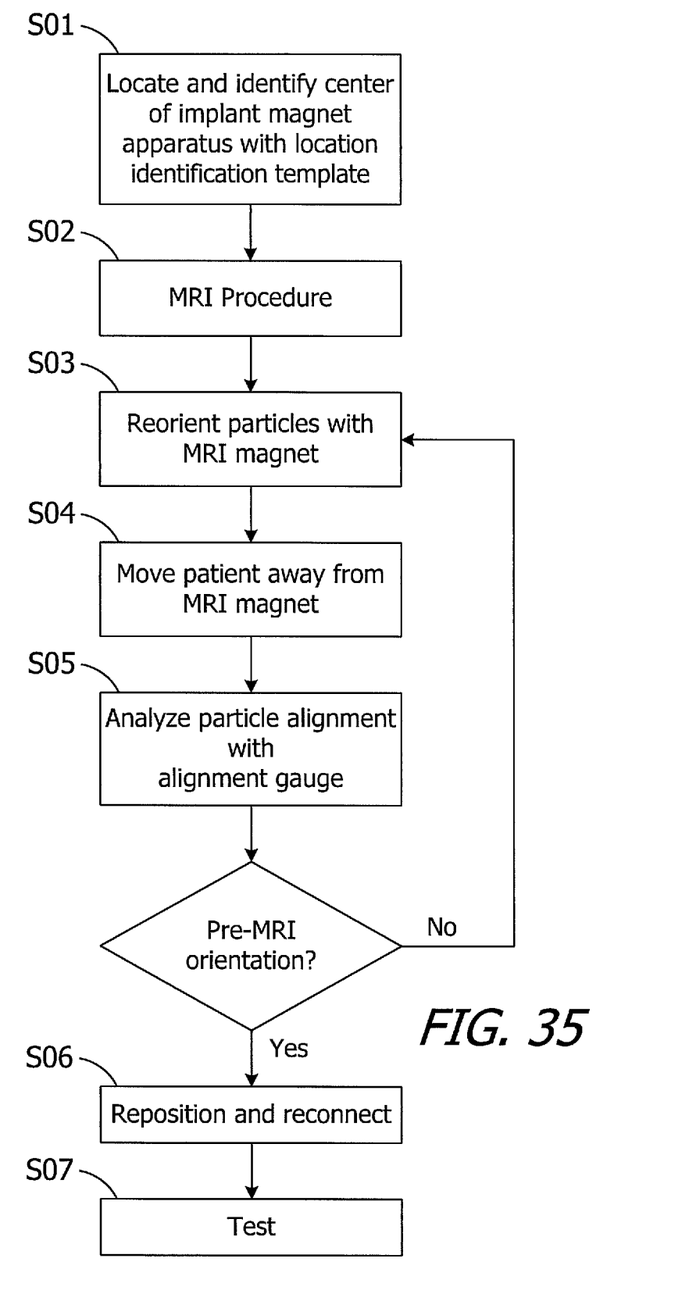
FIG. 35 is a flow chart showing methods steps in accordance with one embodiment of a present invention.

Turning to FIG. 35, the apparatus and methods described above may be employed in conjunction with an MRI procedure being performed on person with a cochlear implant as follows. After the headpiece and any other external portions of the cochlear implant system have been removed, the location identification template 100 (or 100a) of the particle alignment indication kit 70 (or 70a) may be used to locate and identify the center of the MRI-compatible magnet apparatus 30 (Step S01) in the manner described above with reference to FIGS. 12-14 (or FIGS. 25-26). After the location identification template 100 (or 100a) has been removed from the patient's head, the MRI procedure may be performed without removing the magnet apparatus 30 from the patient's head (Step S02).

Upon completion of the MRI procedure, the MRI magnet 52 may be used to reorient the magnetic material particles within the magnet apparatus (Step S03). The patient may be positioned adjacent to the MRI magnet in the manner described above with reference to FIGS. 29-34. At the end of a predetermined period (e.g., 10-15 minutes), the patient may be moved a suitable distance away from the MRI magnet 52 (Step S04) so that the alignment of the magnetic material particles may be evaluated without interference from the MRI magnetic field. Magnetic shielding material may also be placed between the MRI magnet 52 and the patient. Next, the alignment gauge 200 (or 200a) may be used to determine whether or not the magnetic material particles are in their pre-MRI procedure N—S orientations (Step S05) in the manner described above with reference to FIGS. 15-17 (or FIGS. 27-28).

In those instances where the alignment gauge 200 (or 200a) shows that the magnetic material particles are currently in their pre-MRI procedure N—S orientations, the cochlear implant headpiece may be repositioned over the magnet apparatus 30 and, if required by the particular cochlear implant system, reconnected to the sound processor and/or other external components (Step S06). The functionality of the cochlear implant system may then be tested (Step S07). In those instances where the alignment gauge 200 (or 200a) shows that the magnetic material particles are currently in their pre-MRI procedure N—S orientations, Steps S03 to S05 may be repeated.

It should also be noted that, in some implementations, the alignment gauge 200 (or 200a) may be used immediately after the MRI-procedure to determine whether or not the MRI-procedure has caused the magnetic material particles may become misaligned. In those instances where there is no misalignment, the patient may simply move to Step S06. In those instances where there is misalignment, the alignment gauge 200 (or 200a) may be removed and the patient may proceed to Step S03.

In some instances, it may be desirable to reorient the magnetic material particles after an MRI procedure with a device other than the MRI magnet and/or at a facility other than the MRI facility. For example, it may be desirable for an audiologist reorient the magnetic material particles. Here, a magnet that creates a magnetic field of 1.5 Tesla or more, such as those used to perform the initial orientation of the magnetic material particles, may be used to reorient the magnetic material particles.

It should also be noted that although the exemplary MRI system 50 is a closed-type MRI system, the present methods may be performed with an open-type MRI system.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A particle alignment method for use with an MRI system that has a scanning area and that creates an MRI magnetic field, the method comprising the step of:
    positioning a cochlear implant, which is implanted within a patient's head and which includes a magnet apparatus with a central axis and magnetic material particles, at a location that is all three of outside of the scanning area, adjacent to the MRI system, and within the MRI magnetic field created by the MRI system in such a manner that the central axis of the magnet apparatus is at least substantially parallel to the MRI magnetic field.

2. A method as claimed in claim 1, wherein
    the MRI system includes an MRI magnet defining an outer perimeter having a diameter; and
    positioning the cochlear implant comprises positioning the cochlear implant within a cylindrical zone defining an outer perimeter with the same diameter as, and that is aligned with, the outer perimeter of the MRI magnet.

3. A method as claimed in claim 1, further comprising the step of:
    maintaining the cochlear implant at the location outside of the scanning area, adjacent to the MRI system, and within the MRI magnetic field for at least 10 minutes.

4. A method as claimed in claim 1, wherein
    the MRI system includes a patient table; and
    positioning the cochlear implant comprises positioning the cochlear implant while the patient is sitting on the patient table.

5. A method as claimed in claim 1, wherein
    positioning the cochlear implant comprises positioning the cochlear implant while the patient is sitting in a wheelchair.

6. A method as claimed in claim 1, wherein
    positioning the cochlear implant comprises positioning the cochlear implant at the location without a headpiece.

7. A method as claimed in claim 1, wherein
    positioning the cochlear implant comprises positioning the cochlear implant at the location after completion of an MRI procedure.

8. A particle alignment indication kit, comprising:
    a location identification template including a template magnet and at least one aperture; and
    an alignment gauge including a gauge magnet and an at least substantially transparent member associated with the gauge magnet.

9. A particle alignment indication kit as claimed in claim 8, wherein
    the location identification template includes a housing, the template magnet carried by the housing, and the at least one aperture extends through the housing.

10. A particle alignment indication kit as claimed in claim 8, wherein
    the template magnet is selected from the group consisting of a cylindrical template magnet and an annular template magnet.

11. A particle alignment indication kit as claimed in claim 8, wherein
    the at least substantially transparent member includes a reticle.

12. A particle alignment indication kit as claimed in claim 8, wherein
    the alignment gauge includes a frame and the gauge magnet and the at least substantially transparent member are carried by the frame.

13. A particle alignment indication kit as claimed in claim 8, wherein
    the gauge magnet is selected from the group consisting of a cylindrical gauge magnet and an annular gauge magnet.

14. A method for use with a cochlear implant that is implanted under the skin of a patient's head, the cochlear implant including a magnet apparatus with magnetic material particles having a pre-MRI orientation, the method comprising the steps of:
    prior to an MRI procedure where the patient is placed into a scanning area of an MRI system that includes an MRI magnet that creates an MRI magnetic field, placing a location identification template on the patient's head and over the magnet apparatus and making at least one mark on the patient's head based on the position of the location identification template;
    removing the location identification template from the patient's head after the at least one mark has been made and prior to the MRI procedure; and
    after the MRI procedure, placing an alignment gauge on the patient's head and over the magnet apparatus and determining whether or not the magnetic material particles are in the pre-MRI orientation by observing the position of the at least one mark on the patient's head relative to the alignment gauge.

15. A method as claimed in claim 14, wherein
    the location identification template includes a template magnet and at least one aperture; and
    making at least one mark comprises inserting a skin marking instrumentality through the at least one aperture.

16. A method as claimed in claim 14, wherein
    the alignment gauge includes a gauge magnet and an at least substantially transparent member associated with the gauge magnet; and
    observing the position of the at least one mark comprises observing the position of the at least one mark through the at least substantially transparent member.

17. A method as claimed in claim 16, wherein
    the at least substantially transparent member includes a reticle; and
    determining whether or not the magnetic material particles are in the pre-MRI orientation comprises observing the position of the at least one mark on the patient's head relative to the reticle.

18. A method as claimed in claim 14, wherein the magnet apparatus defines a central axis, the method further comprising the step of:

after the MRI procedure and prior to placing the alignment gauge on the patient's head, positioning the patient's head at a location outside of the MRI system scanning area, adjacent to the MRI magnet, and within the MRI magnetic field in such a manner that the MRI magnetic field is at least substantially parallel to the central axis of the magnet apparatus.

19. A method as claimed in claim 14, wherein the magnet apparatus defines a central axis, the method further comprising the step of:

after the MRI procedure, and in response to a determination that the magnetic material particles are in the pre-MRI orientation, removing the alignment gauge from the patient's head and positioning the patient's head at a location outside of the MRI system scanning area, adjacent to the MRI magnet, and within the MRI magnetic field in such a manner that the MRI magnetic field is at least substantially parallel to the central axis of the magnet apparatus.

\* \* \* \* \*